(12) United States Patent
Iizuka et al.

(10) Patent No.: US 10,271,715 B2
(45) Date of Patent: Apr. 30, 2019

(54) DISTAL END COVER OF ENDOSCOPE AND ENDOSCOPE

(71) Applicant: OLYMPUS CORPORATION, Tokyo (JP)

(72) Inventors: Tomoyuki Iizuka, Hachioji (JP); Akihiro Kato, Hino (JP)

(73) Assignee: OLYMPUS COPORATION, Tokyo (JP)

( * ) Notice: Subject to any disclaimer, the term of this patent is extended or adjusted under 35 U.S.C. 154(b) by 0 days.

(21) Appl. No.: 15/591,312

(22) Filed: May 10, 2017

(65) Prior Publication Data
US 2017/0238789 A1  Aug. 24, 2017

Related U.S. Application Data

(63) Continuation of application No. PCT/JP2016/060684, filed on Mar. 31, 2016.

(30) Foreign Application Priority Data

Jul. 15, 2015 (JP) .................................. 2015-141534

(51) Int. Cl.
A61B 1/00 (2006.01)
A61B 1/018 (2006.01)
A61B 90/00 (2016.01)

(52) U.S. Cl.
CPC ...... *A61B 1/00137* (2013.01); *A61B 1/00089* (2013.01); *A61B 1/00098* (2013.01);
(Continued)

(58) Field of Classification Search
CPC ............ A61B 1/00137; A61B 1/00098; A61B 1/00101; B65D 41/32; Y10S 604/905
(Continued)

(56) References Cited

U.S. PATENT DOCUMENTS 5,147,305 A * 9/1992 Nakamura ......... A61B 1/00062
604/110
5,359,991 A * 11/1994 Takahashi .......... A61B 1/00142
359/510

(Continued)

FOREIGN PATENT DOCUMENTS

CN 101061940 A 10/2007
EP 1 849 397 A1 10/2007
(Continued)

OTHER PUBLICATIONS

International Search Report dated Jun. 28, 2016 issued in PCT/JP2016/060684.

(Continued)

*Primary Examiner* — Timothy J Neal
*Assistant Examiner* — Jae Woo
(74) *Attorney, Agent, or Firm* — Scully, Scott, Murphy & Presser, P.C.

(57) ABSTRACT

A distal end cover of an endoscope includes a peripheral edge portion configured to form an opening that externally exposes a space in which a raising base is housed, in a distal end member; a planned-to-be-torn-apart section including a tear starting point disposed on the peripheral edge portion, and a thin portion that is connected to a to-be-torn-apart section of the peripheral edge portion torn from the tear starting point, on an inside surface of a surface facing the opening or an inside surface of at least one side surface that connects the peripheral edge portion and the surface facing the opening; and an engagement portion configured to be engaged with an outside surface of the distal end member by engaging in a direction intersecting the outside surface.

9 Claims, 9 Drawing Sheets

(52) U.S. Cl.
CPC ...... *A61B 1/00101* (2013.01); *A61B 1/00135* (2013.01); *A61B 1/018* (2013.01); *A61B 2090/037* (2016.02)

(58) Field of Classification Search
USPC .......................................................... 600/107
See application file for complete search history.

(56) References Cited

U.S. PATENT DOCUMENTS

| | | | | |
|---|---|---|---|---|
| 5,569,157 | A * | 10/1996 | Nakazawa | A61B 1/0008 600/104 |
| 5,738,630 | A * | 4/1998 | Suzuki | A61B 1/00057 600/121 |
| 5,860,913 | A | 1/1999 | Yamaya et al. | |
| 5,868,663 | A * | 2/1999 | Katsurada | A61B 1/0008 600/106 |
| 6,605,033 | B1 * | 8/2003 | Matsuno | A61B 1/00098 600/106 |
| 7,762,949 | B2 * | 7/2010 | Nakao | A61B 1/00073 600/104 |
| 8,038,604 | B2 | 10/2011 | Hamazaki et al. | |
| 2006/0287578 | A1 * | 12/2006 | Hamazaki | A61B 1/00062 600/154 |
| 2007/0246506 | A1 | 10/2007 | Hamazaki et al. | |
| 2008/0183038 | A1 * | 7/2008 | Tilson | A61B 1/018 600/104 |
| 2010/0305404 | A1 | 12/2010 | Ushijima et al. | |
| 2017/0000317 | A1 * | 1/2017 | Iizuka | A61B 1/00 |
| 2017/0000319 | A1 * | 1/2017 | Iizuka | A61B 1/00 |

FOREIGN PATENT DOCUMENTS

| | | |
|---|---|---|
| JP | H08-140924 A | 6/1996 |
| JP | H09-299315 A | 11/1997 |
| JP | H10-216075 A | 8/1998 |
| JP | 2002-017654 A | 1/2002 |
| JP | 2003-102668 A | 4/2003 |
| JP | 4855824 B2 | 1/2012 |

OTHER PUBLICATIONS

Extended Supplementary European Search Report dated Jun. 18, 2018 in European Patent Application No. 16 82 4113.1.

* cited by examiner

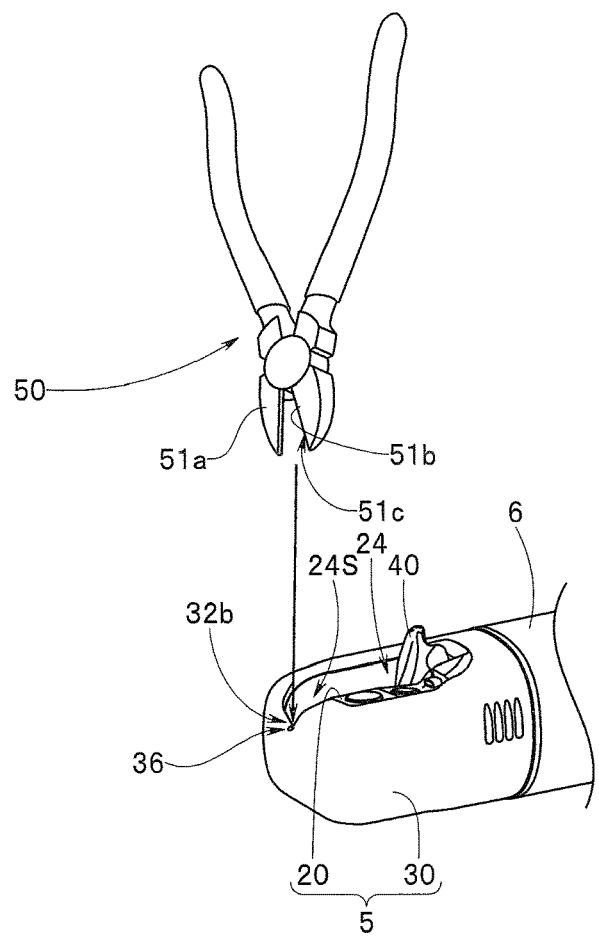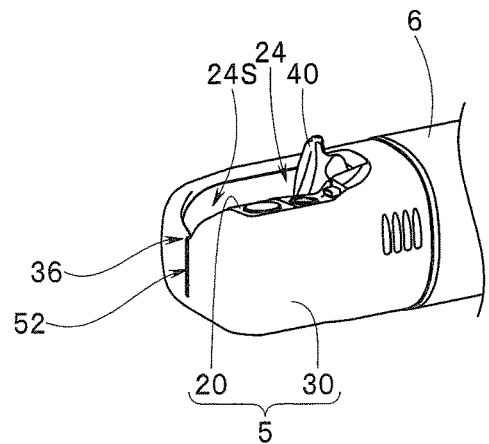

DISTAL END COVER OF ENDOSCOPE AND ENDOSCOPE

CROSS REFERENCE TO RELATED APPLICATION

This application is a continuation application of PCT/JP2016/060684 filed on Mar. 31, 2016 and claims benefit of Japanese Application No. 2015-141534 filed in Japan on Jul. 15, 2015, the entire contents of which are incorporated herein by this reference.

BACKGROUND OF THE INVENTION

1. Field of the Invention

The present invention relates to a distal end cover of an endoscope, which is attached to a distal end member provided with a raising base that configures a distal end portion of an endoscope insertion portion, and an endoscope to which a distal end cover is attached.

2. Description of the Related Art

One medical endoscope is a side-view type endoscope (hereinafter, referred to as an endoscope) in which an illumination lens and an objective lens are arranged on a distal end-side side surface of an insertion portion, a so-called duodenoscope.

The endoscope is provided with a treatment instrument channel and a raising apparatus.

A treatment instrument such as a contrast tube, a basket catheter, or a balloon catheter is inserted into the treatment instrument channel. The treatment instrument that passes through the treatment instrument channel is drawn out from a distal end opening provided in a distal end member, and a drawing out direction is switched to a desired direction by the raising apparatus.

The raising apparatus is typically configured mainly by a raising base rotatably arranged on the distal end member, a raising base operation lever provided on an operation portion, and a raising base operation wire that moves in accordance with an operation of the raising base operation lever and swings the raising base.

Also, a distal end cover of an endoscope, which is electrically insulated, is provided on an exterior of the distal end member. The distal end cover is fixed by adhesive or the like to prevent the distal end cover from falling off the distal end member.

The endoscope is cleaned and disinfected after use. It is known that when cleaning an insertion portion of an endoscope, cleaning can be easily performed by removing the distal end cover from the distal end portion to expose a distal end opening of the treatment instrument channel.

For example, Japanese Patent No. 4855824 describes an endoscope distal end cover, an endoscope apparatus, and a method for removing a distal end cover of an endoscope in an endoscope apparatus, which enables an endoscope distal end cover to be removed from a distal end member by ripping and breaking up the endoscope distal end cover, without damaging a flexible member that configures an insertion portion, and is able to prevent the endoscope distal end cover from falling off during use.

The endoscope distal end cover is provided with a concave groove and a thin portion that is a plastic deformation portion for sequentially releasing an engagement state by a first engagement portion, a second engagement portion, and a third engagement portion, by causing plastic deformation starting at a finger-hooking portion.

The thin portion is provided on a side surface portion between an open portion and the finger-hooking portion of the distal end cover of the endoscope.

The concave groove is formed on an inner peripheral surface along an entire periphery from a proximal end portion of the thin portion, or near the proximal end portion, to a side surface portion, a front surface portion, and a side surface portion on the opposite side, of the endoscope distal end cover.

SUMMARY OF THE INVENTION

A distal end cover of an endoscope according to one aspect of the present invention is a distal end cover of an endoscope, which is attached to a distal end member provided with a raising base of an endoscope insertion portion, including a peripheral edge portion configured to form an opening that externally exposes a space in which the raising base is housed, in the distal end member; a planned-to-be-torn-apart section including a tear starting point disposed on the peripheral edge portion, and a thin portion that is connected to a to-be-torn-apart section of the peripheral edge portion torn from the tear starting point, on an inside surface of a surface facing the opening or an inside surface of at least one side surface that connects the peripheral edge portion and the surface facing the opening; and an engagement portion configured to be engaged with an outside surface of the distal end member by engaging in a direction intersecting the outside surface.

A distal end cover of an endoscope according to one aspect of the present invention is a distal end cover of an endoscope, which is attached to a distal end member provided with a raising base that configures a distal end portion of an endoscope insertion portion, including a peripheral edge portion configured to form an open portion that exposes a space in which the raising base is housed; an engagement portion configured to be engaged with the distal end member; and a planned-to-be-torn-apart section including a tear starting point that is provided on a distal end cover distal end surface side of the peripheral edge portion, and is configured to be torn when an engagement state in which the engagement portion is engaged with the distal end member is released, and a thin portion that is provided extending along a longitudinal axis of the endoscope insertion portion from the distal end cover distal end surface side to a proximal end portion, on an inside surface of another surface facing one surface that includes the peripheral edge portion.

An endoscope according to one aspect of the present invention includes an engageable portion configured to engage with an engagement portion of a distal end cover of an endoscope, which is attached to a distal end member provided with a raising base of an endoscope insertion portion and includes a peripheral edge portion configured to form an opening that externally exposes a space in which the raising base is housed, in the distal end member; a planned-to-be-torn-apart section including a tear starting point disposed on the peripheral edge portion, and a thin portion that is connected to a to-be-torn-apart section of the peripheral edge portion torn from the tear starting point, on an inside surface of a surface facing the opening or an inside surface of at least one side surface that connects the peripheral edge portion and the surface facing the opening; and the engagement portion configured to be engaged with an outside surface of the distal end member by engaging in a direction intersecting the outside surface.

BRIEF DESCRIPTION OF THE DRAWINGS

FIG. 7A is a view illustrating a procedure for disposing a cutting instrument in a space for cutting of a cover;

FIG. 7B is a view illustrating a cut formed in the cover distal end surface of the cover;

DETAILED DESCRIPTION OF THE PREFERRED EMBODIMENT(S)

Figure 1:
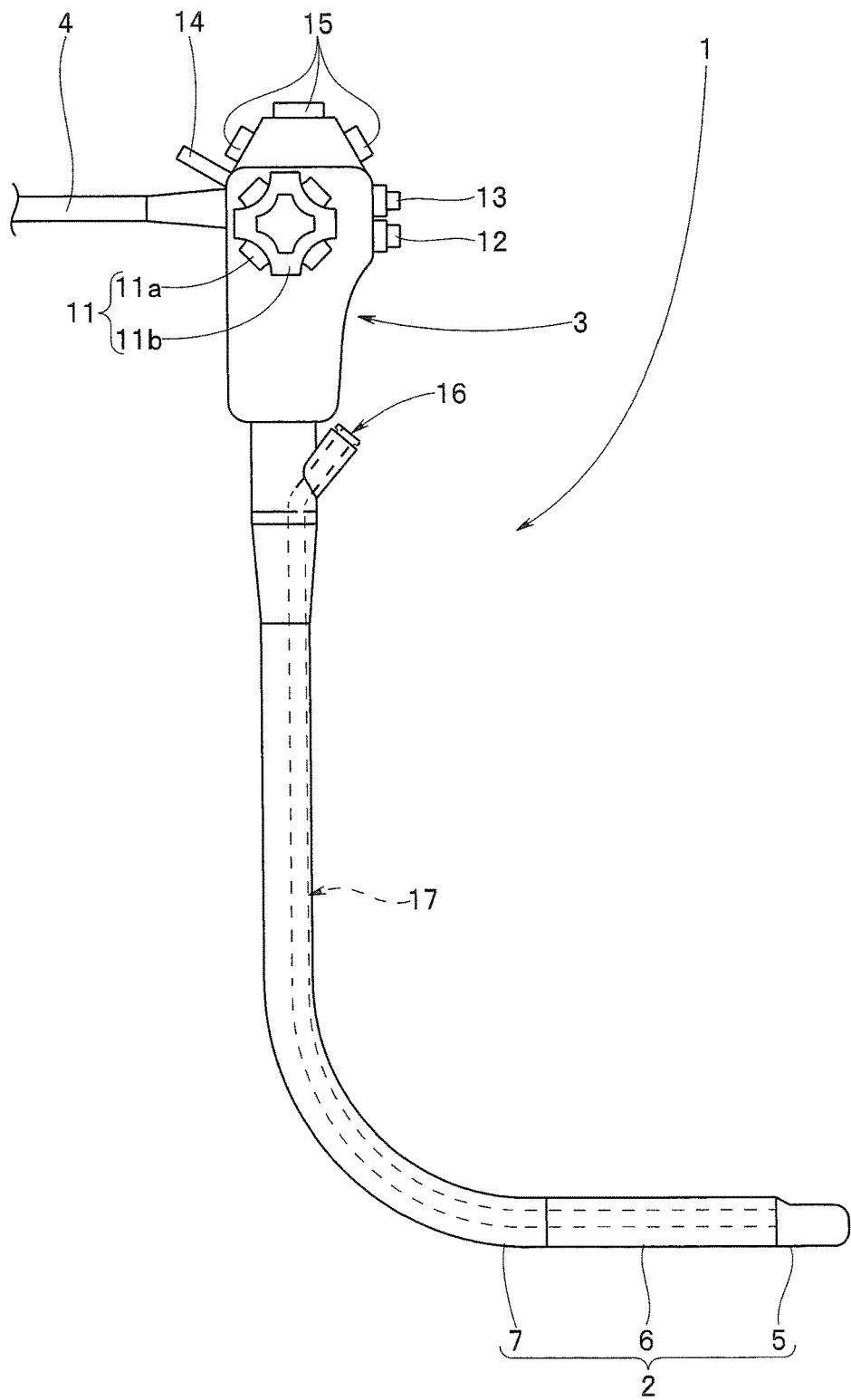
FIG. 1 is a view illustrating a side-view type endoscope.

Hereinafter, an embodiment of the present invention will be described with reference to drawings.

Note that in the respective drawings used in the description below, in order to make sizes of respective constituent elements recognizable in the drawings, a scale size may be different for each constituent element. Also, the present invention is not limited to only the number of constituent elements, the shapes of constituent elements, the size ratios of constituent elements, and relative positional relationships of respective constituent elements shown in the drawings.

In the embodiment, an endoscope is a side-view type endoscope. A distal end cover is a distal end cover of the side-view type endoscope, which is attached to the side-view type endoscope.

As shown in FIG. 1, an endoscope 1 includes an insertion portion 2 that is inserted into a subject, an operation portion 3 that is provided on a proximal end side of the insertion portion 2, and a universal cord 4 that extends from the operation portion 3.

The operation portion 3 of the endoscope 1 is provided with a bending operation apparatus 11, an air/water feeding button 12, a suction button 13, a raising base operation lever 14, and various operation switches 15.

The operation switches 15 are a freeze switch that generates a freeze signal, a release switch that generates a release signal when shooting photography, and an observation mode switching switch for giving a command to switch an observation mode, and the like.

The operation portion 3 is provided with a treatment instrument insertion opening 16 for introducing a treatment instrument (not shown) in-vivo. One end side of a treatment instrument channel tube 17 is connected to the treatment instrument insertion opening 16. The other end side of the treatment instrument channel tube 17 is connected to a distal end member (see reference numeral 20 in FIG. 2 and the like) that configures a distal end portion 5 of the insertion portion 2.

The insertion portion 2 that is extending from the operation portion 3 includes, connected continuously, the distal end portion 5, a bending section 6, and a flexible tube section 7, in order from the distal end side.

The flexible tube section 7 includes, for example, a helical tube, a mesh tube that covers the helical tube, and a heat shrinkable tube that configures an outermost layer, none of which are shown. The bending section 6 includes, for example, a pair of bending pieces configured to bend in four directions, i.e., up, down, left, and right, a mesh tube made of metal that covers the pair of bending pieces, and bending rubber that is an outer skin.

The bending section 6 is configured to bend in an up direction or a down direction by a rotatably operating an up/down bending knob 11a of the bending operation apparatus 11 provided on the operation portion 3, and bend in a left direction or a right direction by rotatably operating a left/right bending knob 11b.

Figure 2:
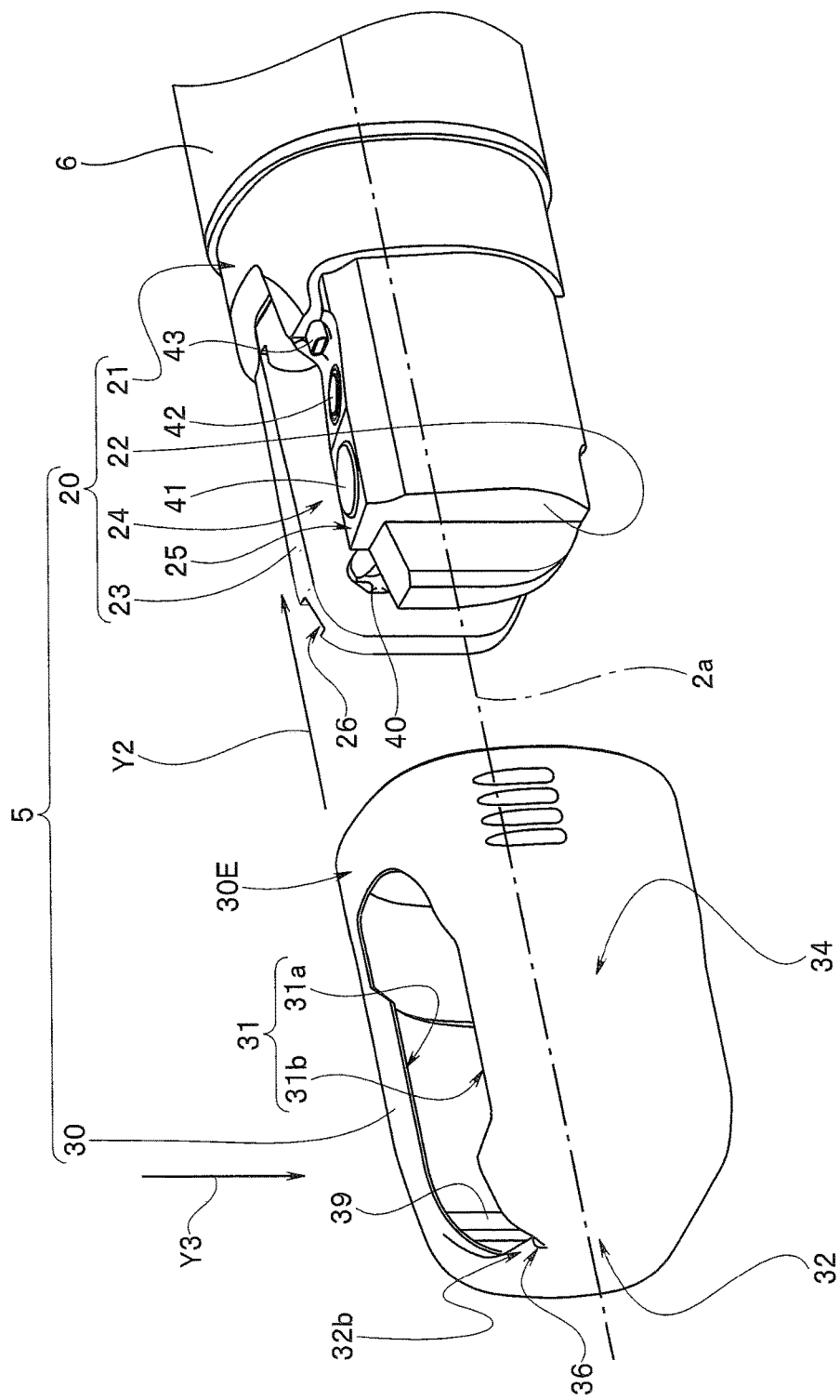
FIG. 2 is a view illustrating a distal end cover and a distal end member that configures a distal end portion of an insertion portion of the endoscope.

As shown in FIG. 2, the distal end portion 5 is configured with a distal end cover (hereinafter, simply referred to as a cover) 30 of the endoscope attached to the distal end member 20.

The distal end member 20 is a rigid member that configures the distal end portion 5, and the cover 30 is made of resin, for example, having an electrical insulating property, and has a predetermined resilient property.

The distal end member 20 includes a distal end portion main body 21 that is made of resin and has an electrical insulating property, and an optical protruding portion 22 made of metal and a protruding portion for raising 23 similarly made of metal, which protrude toward the distal end side along an insertion portion longitudinal axis 2a from the distal end portion main body 21. A gap between the optical protruding portion 22 and the protruding portion for raising 23 is a raising base housing space 24 in which a raising base 40 is rotatably housed and disposed.

The raising base 40 is a rigid member and is made of metal or resin.

Figure 5:
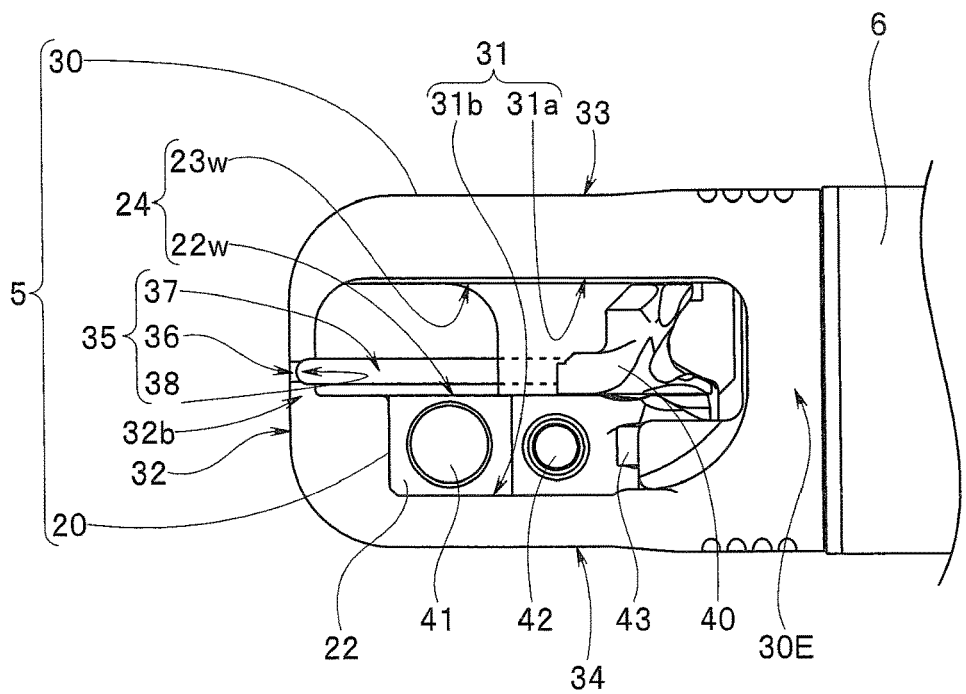
FIG. 5 is a front view of the distal end portion viewed from a direction of arrow Y5 in FIG. 4A.

More specifically, the raising base 40 is disposed between a first wall surface 22w and a second wall surface 23w that are face-to-face and configure the raising base housing space 24 as shown in FIG. 5, and rotates freely. The first wall surface 22w is an inside surface wall of the optical protruding portion 22, and the second wall surface 23w is an inside surface wall of the protruding portion for raising 23.

As shown in FIG. 2 and FIG. 5, an illumination lens 41 and an observation lens 42 are provided in predetermined positions on an upper surface 25 that is one surface of the optical protruding portion 22. Reference numeral 43 denotes a cleaning nozzle.

Fluid is sprayed from the cleaning nozzle 43. Filth adhering to the surface of the illumination lens 41 and the surface of the observation lens 42 is removed by the fluid sprayed from the cleaning nozzle 43.

Figure 6:
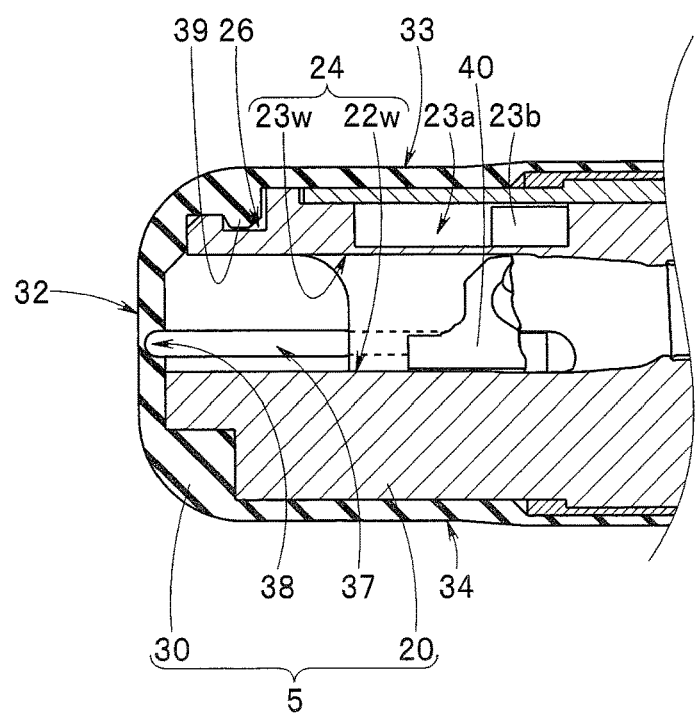
FIG. 6 is a sectional view taken along line depicted by arrow Y6-Y6 in FIG. 4A, illustrating an engagement portion of the distal end cover and the distal end member.

An arm recess portion (see reference character 23a in FIG. 6), and an engagement groove 26 that configures one of engagement portions, are formed on the protruding portion for raising 23. An engagement protruding portion 39 that will be described later is disposed engaged in the engagement groove 26.

A raising base moving arm 23b is arranged inside the arm recess portion 23a. A shaft portion (not shown) fixed to the raising base 40 is provided on the raising base moving arm. The shaft portion comes out from within the arm recess portion into the raising base housing space 24 through a through-hole (not shown), and is integrally fixed to the raising base 40.

The arm recess portion 23a does not have to be formed on the protruding portion for raising 23. In this case, the raising base moving arm 23b is not disposed, and a raising base operation wire is directly connected to the raising base 40.

Note that the upper surface refers to a surface that corresponds to the upper bending direction of the bending section 6.

On the other hand, an opening 31 is provided in an upper surface that is one surface of the cover 30. The opening 31 has a first open portion 31a and a second open portion 31b, and is formed as a single opening. That is, a portion of the first open portion 31a and a portion of the second open portion 31b are connected together, thereby configuring the opening 31.

The first open portion 31a has a generally rectangular shape, and is a raising base open portion that exposes the raising base housing space 24 provided in the distal end member 20, and from which the raising base 40 protrudes and recedes.

In contrast, the second open portion 31b has a generally rectangular shape, and is a lens exposing open portion that exposes the illumination lens 41 and the observation lens 42 provided on the upper surface 25 of the distal end member 20.

A cover distal end surface denoted by reference numeral 32, a cover left side surface denoted by reference numeral 33, and a cover right side surface denoted by reference numeral 34, are provided between the upper surface of the cover 30 and a lower surface that is the other surface facing the upper surface.

The cover distal end surface 32 is a distal-most end surface of the insertion portion 2. The cover left side surface 33 is one side surface positioned on the left side when the cover distal end surface 32 is viewed from the front, and the cover right side surface 34 is the other side surface positioned on the right side opposite to the cover left side surface 33 with the insertion portion longitudinal axis 2a being sandwiched.

Figure 3:
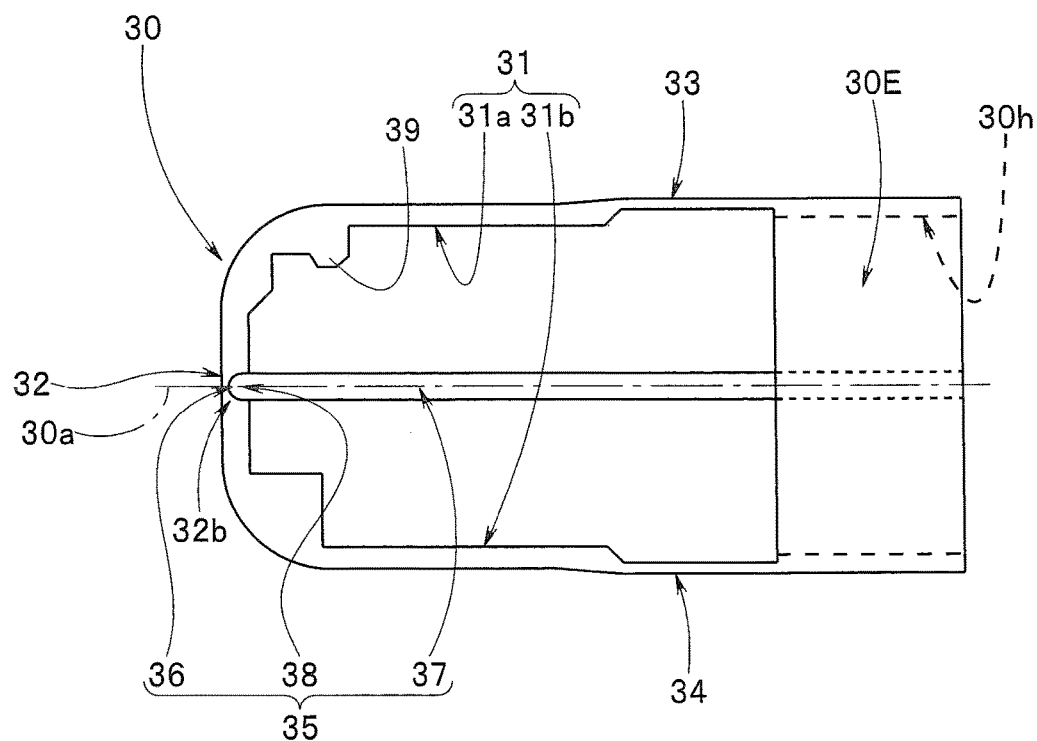
FIG. 3 is a front view of the distal end cover viewed from a direction of arrow Y3 in FIG. 2.

As shown in FIG. 2 and FIG. 3, a planned-to-be-torn-apart section 35 and the engagement protruding portion 39 are provided on an inside surface of the cover 30.

In the present embodiment, the planned-to-be-torn-apart section 35 has a tear starting point 36, a first thin portion 37, and a second thin portion 38.

The tear starting point 36 is a notch portion provided on an inside surface of the first open portion 31a and a peripheral edge portion 32b on the cover distal end surface 32 side. The tear starting point 36 is also an indicating portion that indicates a tear point that is to be torn first when removing the cover 30 from the distal end member 20.

The first thin portion 37 is a first groove provided along the insertion portion longitudinal axis 2a on an inside surface of a lower surface that faces the first open portion 31a. The first groove is V-shaped, semicircular-shaped, or concave-channel-shaped, and a groove distal end is positioned on an inside surface of the cover distal end surface 32.

The second thin portion 38 is a second groove provided on an inside surface of the cover distal end surface 32, and is formed so as to continuously connect with the groove distal end of the first groove from the tear starting point 36. The shape of the second groove is a shape similar to the shape of the first groove, and is V-shaped, semicircular-shaped, or concave-channel-shaped.

The engagement protruding portion 39 is a protruding portion that configures the other of the engagement portions, and is provided to a distal end side with respect to the opening 31. More specifically, the engagement protruding portion 39 is provided in a position a predetermined distance away from the inside surface of the cover distal end surface 32, on the inside surface of the cover left side surface 33. In other words, the tear starting point 36 is positioned to a distal end side of the insertion portion longitudinal axis 2a with respect to the engagement protruding portion 39.

The engagement protruding portion 39 is disposed engaged in the engagement groove 26. Also, the engagement protruding portion 39 is shaped protruding a predetermined height from an inside surface, and with a predetermined width, so as to be disposed engaged in a predetermined state with respect to the engagement groove 26.

Note that reference character 30E denotes an attaching section, and is an annular portion having a predetermined resilient property. Reference character 30h denotes a connecting hole that is a through-hole formed in the attaching section 30E.

Figure 4A:
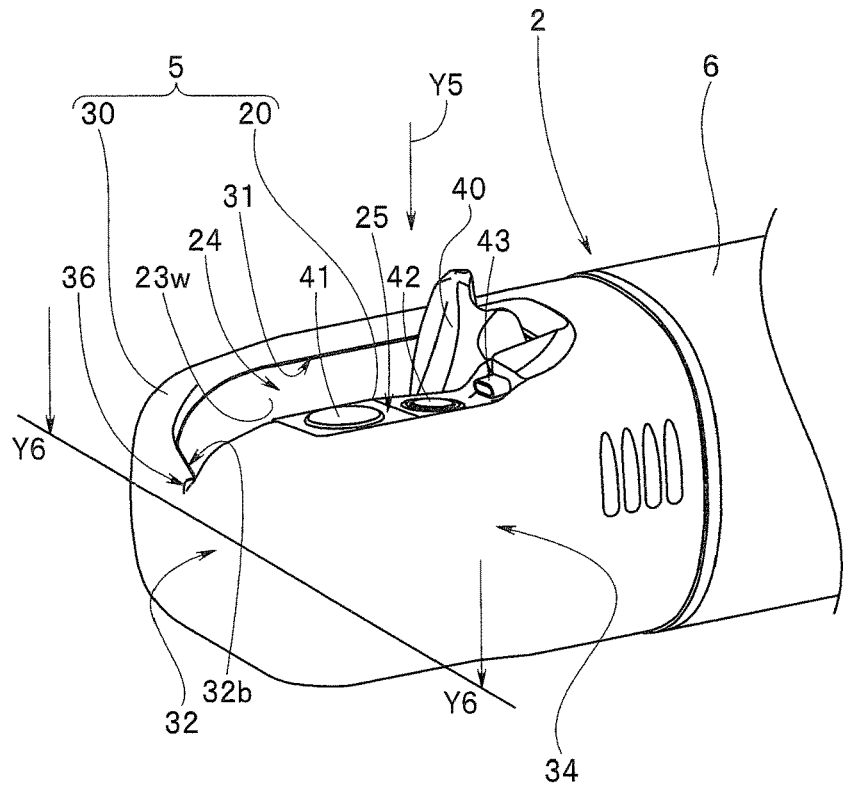
FIG. 4A is a perspective view showing the distal end portion in which the distal end cover is attached to the distal end member.
Figure 4B:
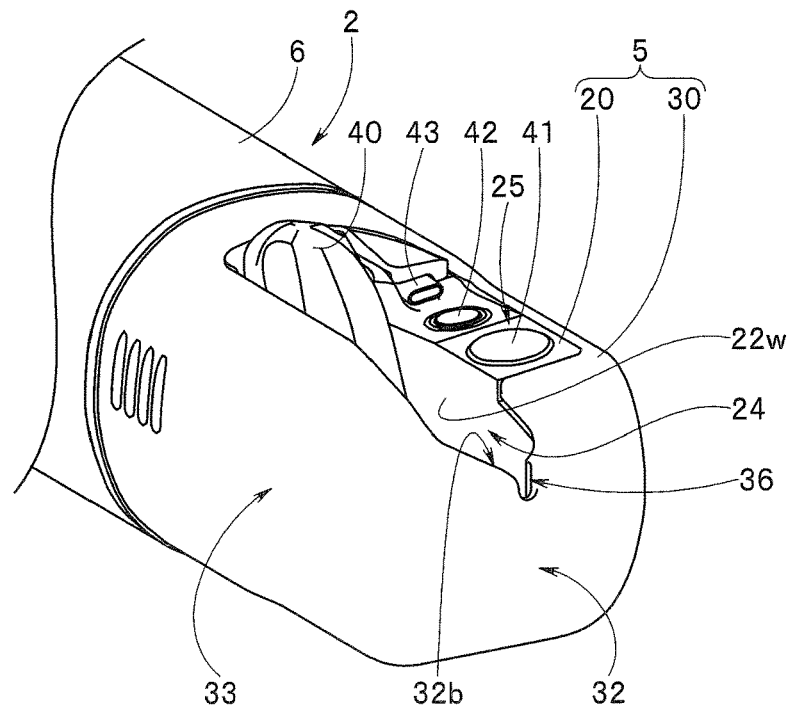
FIG. 4B is a perspective view showing the distal end portion in which the distal end cover is attached to the distal end member, viewed from a different angle.

As shown by arrow Y2 in FIG. 2, the cover 30 is disposed on and covers the distal end member 20, and configures the distal end portion 5 shown in FIG. 4A to FIG. 5.

At this time, an inner peripheral surface of the connecting hole 30h provided in the attaching section 30E is disposed in close contact with an outer peripheral surface of the distal end portion main body 21, by the resilient force of the attaching section 30E. In addition, the engagement protruding portion 39 is disposed engaged in the engagement groove 26, and is thus in an engagement state.

As a result, the distal end portion 5 in which the cover 30 is reliably fixed to the distal end member 20 is configured. In this fixed state, a large part of the planned-to-be-torn-apart section 35 provided on the first open portion 31a of the opening 31 is disposed in a position away from a metal portion of the distal end member 20.

Here, removal of the cover 30 will be described with reference to FIG. 7A to FIG. 7D.

An operator wears gloves when cleaning and disinfecting the endoscope 1 after use. Also, an operator prepares nippers, for example, as a cutting instrument, in advance.

When starting a cleaning operation, an operator first hand-side operates the raising base operation lever 14, and places the raising base 40 that is disposed inverted inside the raising base housing space 24 in a raised state. As a result, a cutting instrument disposing space 24S is provided on the distal end side of the raising base housing space 24.

In this way, the cutting instrument disposing space 24S is able to be provided in the raising base housing space 24 by placing the raising base 40 in a raised state. As a result, the position of the second thin portion 38 and the position of the first thin portion 37 provided on the cover 30 are able to be easily confirmed visually without being blocked by the raising base 40.

Next, as shown in FIG. 7A, the operator disposes blades 51a, 51b of nippers 50 near the tear starting point 36 of the cover 30 as shown by the arrow, and performs a cutting operation. At this time, the operator disposes one blade 51b inside the cutting instrument disposing space 24S, and disposes the blade 51b along the first wall surface 22w, and cuts with a blade face 51c along the second thin portion 38.

As a result, a cut 52 that is a to-be-torn-apart section is formed in the cover distal end surface 32, as shown in FIG. 7B.

In this way, by providing the tear starting point 36 on the peripheral edge portion 32b, the operator is able to easily grasp the portion to be torn apart first with the nippers 50. Also, by providing the second thin portion 38 on the inside surface of the cover distal end surface 32, the operator is able to cut with little strength along the second thin portion 38 and form the cut 52 in the cover distal end surface 32.

Next, the operator clamps and holds the cover left side surface 33 side of the cover distal end surface 32 with the blades 51a, 51b of the nippers 50. Here, the operator performs a hand-side operation to move the nippers 50 as indicated by the arrow, and rips (tears apart) the cover distal end surface 32 held by the nippers 50 as shown by the broken line.

Figure 7C:
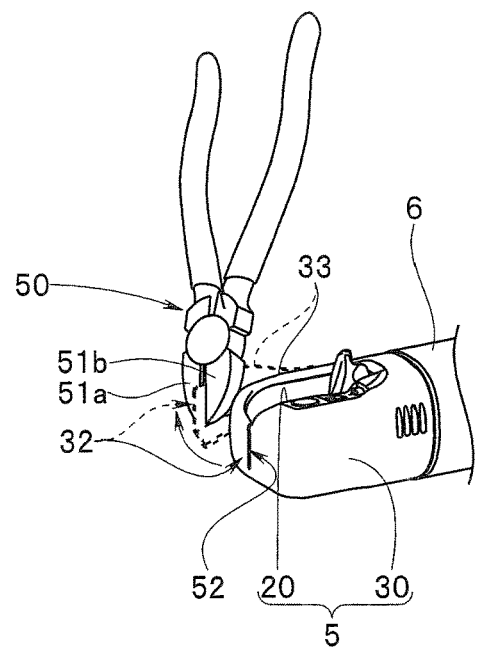
FIG. 7C is a view illustrating a state in which the cover is being ripped using the cutting instrument.
Figure 7D:
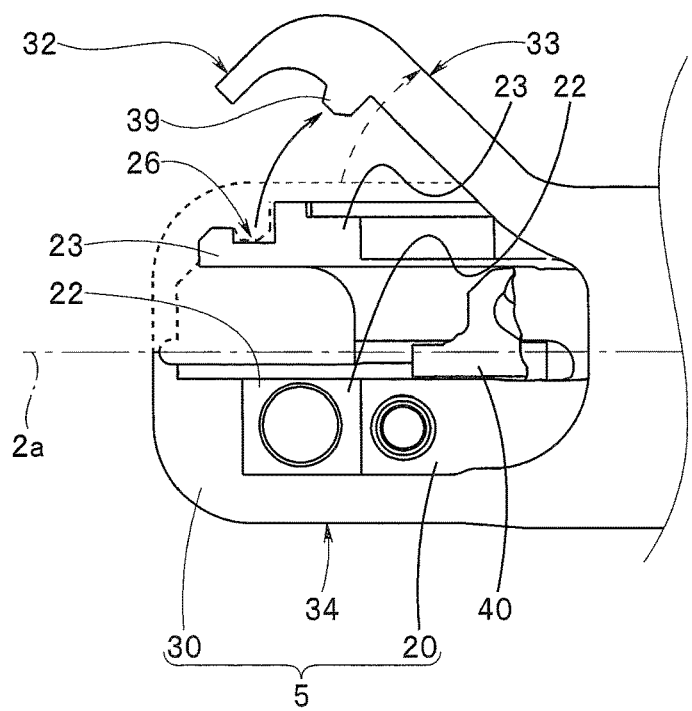
FIG. 7D is a view illustrating a state in which the cover is ripped and an engagement protruding portion is removed from an engagement groove.

At this time, the cover 30 is gradually ripped along the second thin portion 38 and the first thin portion 37, and a portion of the cover 30 is broken up while being extended out so as to gradually move away from the insertion portion longitudinal axis 2a, as shown by the broken arrow in FIG. 7D.

As a result, the engagement protruding portion 39 is removed from the engagement groove 26 as shown by the solid arrow, such that the engagement state is released. Then, the operator rips the cover 30 along the first thin portion 37. As a result, the cover 30 is removed from the distal end portion main body 21. Then, the operator moves onto the cleaning operation.

In this way, the planned-to-be-torn-apart section 35 that includes the tear starting point 36, the first thin portion 37, and the second thin portion 38 is provided at the first open portion 31a of the opening 31 that is provided on the cover 30. As a result, when the distal end portion 5 is configured with the distal end member 20 covered by the cover 30, a large part of the planned-to-be-torn-apart section 35 that is provided on the cover 30 is provided in the raising base housing space 24.

Therefore, when removing the cover 30 from the distal end member 20, the operator is able to dispose the cutting instrument in the cutting instrument disposing space 24S provided on the distal end side of the raising base housing space 24 without damaging the bending rubber that configures the insertion portion 2.

As a result, the operator is able to easily remove the cover 30 from the distal end member 20 by breaking up the cover 30 as described above, using a cutting instrument with gloved fingers.

Note that in the embodiment described above, the second thin portion 38 is provided on the inside surface of the cover distal end surface 32. However, the planned-to-be-torn-apart section 35 may also be configured by the tear starting point 36 and the first thin portion 37.

According to this configuration, the cut 52 can be formed by easily cutting the cover distal end surface 32 with a little strength from the tear starting point 36 with the nippers, by setting the thickness of the cover distal end surface 32 taking cutting easiness into account.

Also, after the cut is formed, the operator can clamp and hold the cover left side surface 33 side of the cover distal end surface 32 with the blades 51a, 51b of the nippers 50, and rip and break up the cover 30 just as described above.

Also, in the embodiment described above, the cover left side surface 33 side of the cover distal end surface 32 is clamped and held by the blades 51a, 51b of the nippers 50, and the cover distal end surface 32 that is held by the nippers 50 is ripped.

Figure 8A:
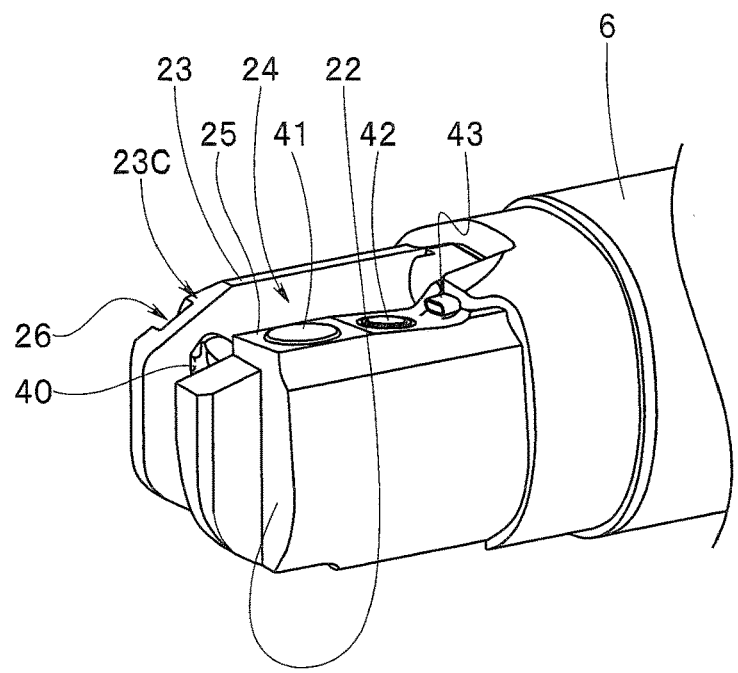
FIG. 8A is a view illustrating a notch surface formed on a protruding portion for raising of a distal end member.
Figure 8B:
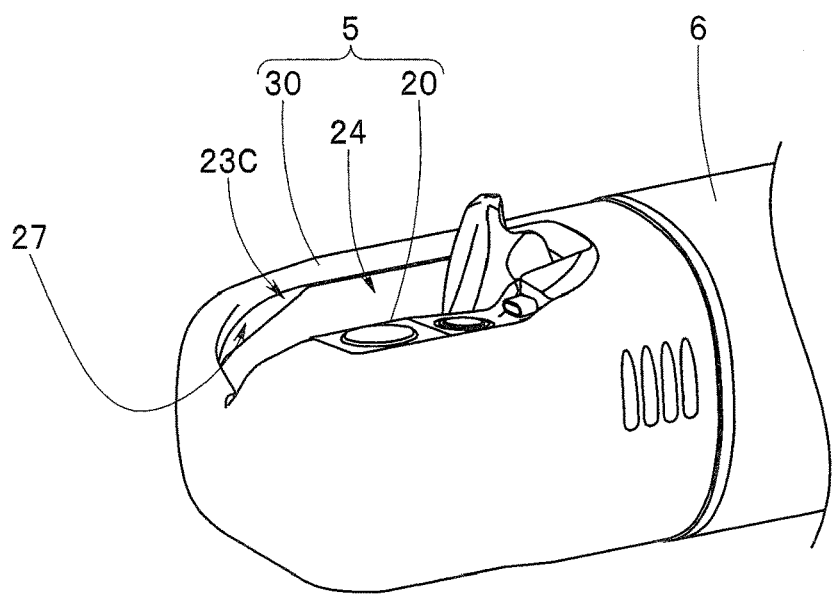
FIG. 8B is a view illustrating a depression in which a fingertip is able to be placed, provided on a distal end portion.

However, by forming a notch surface 23C having a predetermined shape on the distal end side of the protruding portion for raising 23, as shown in FIG. 8A, a depression 27 in which a fingertip is able to be placed may also be provided between the inside surface of the cover 30 and the notch surface 23C, as shown in FIG. 8B, on the distal end portion 5.

Note that the other components are the same as the components in the embodiment described above, so like members are denoted by like reference numerals, and descriptions of these members will be omitted.

According to this configuration, after forming the cut 52 with the nippers or the like, fingers can be placed in and near the depression 27, and the cover left side surface 33 side of the cover distal end surface 32 can be held, and the cover 30 can be ripped and broken up without using the nippers or the like.

Figure 9A:
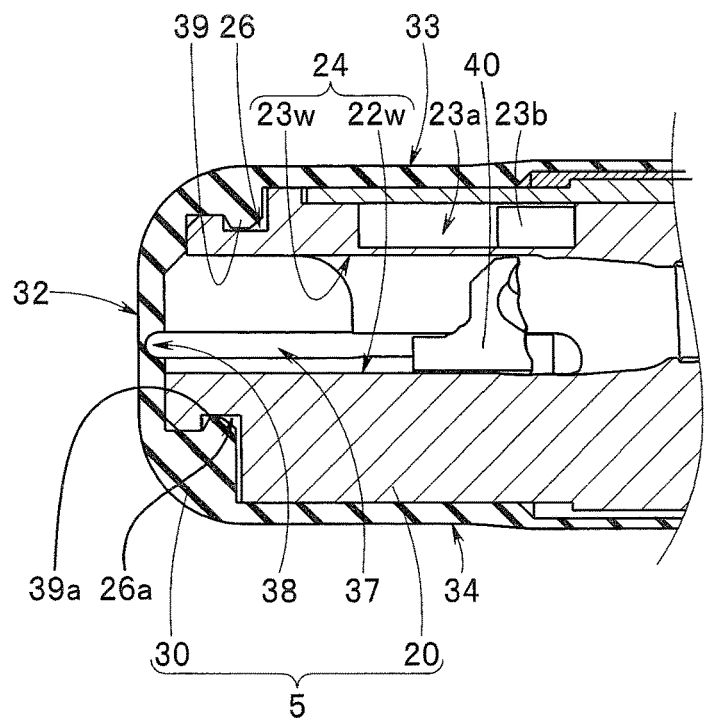
FIG. 9A is a view illustrating the distal end portion provided with two engagement portions.

Also, in the embodiment described above, the engagement protruding portion 39 is provided on the inside surface of the cover left side surface 33. However, an engagement protruding portion 39a may be provided on the inside surface of the cover right side surface 34 as well as on the inside surface of the cover left side surface 33, as shown in FIG. 9A.

Figure 9B:
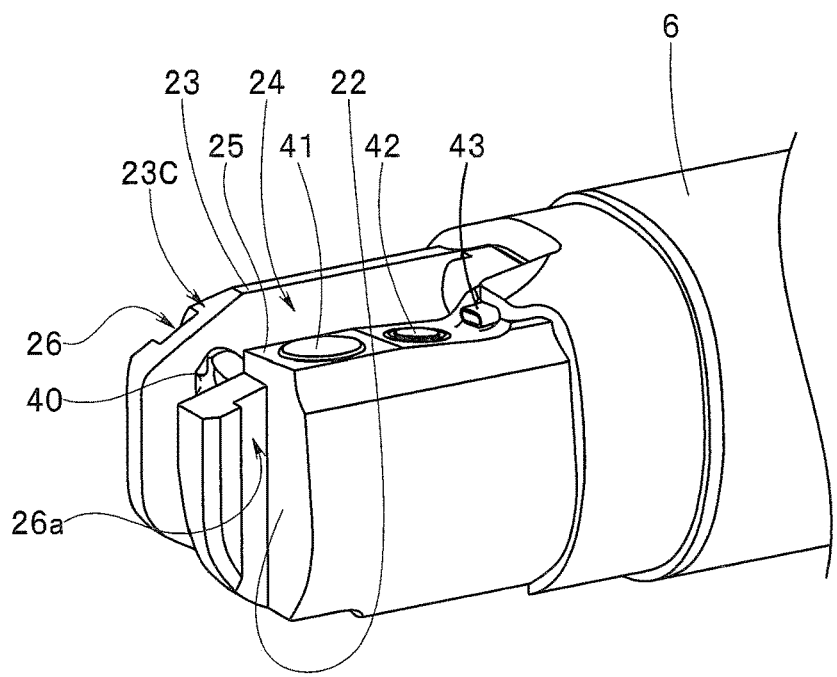
FIG. 9B is a view illustrating the engagement groove provided on the distal end member.

That is, the engagement protruding portions 39, 39a may be provided on the inside surfaces of both side surfaces 33, 34 of the cover 30, respectively. In this case, an engagement groove 26a corresponding to the engagement protruding portion 39a of the cover right side surface 34 is provided in addition to the engagement groove 26 corresponding to the engagement protruding portion 39 of the cover left side surface 33, on the distal end member 20, as shown in FIG. 9B.

Note that the other components are the same as the components in the embodiment described above, so like members are denoted by like reference numerals, and descriptions of these members will be omitted.

According to this configuration, the cover 30 is able to be reliably fixed by the distal end member 20.

Note that the present invention is not limited to only the embodiment described above. Various modifications may also be implemented without departing from the scope of the invention.

For example, the first thin portion 37 described in the foregoing embodiment may also be disposed parallel to the longitudinal axis 2a on a side surface of the cover 30. In this case, the second thin portion 38 need only be disposed so as to extend obliquely toward the inside of the front surface of the cover 30, so as to connect the tear starting point 36 with the first thin portion 37.

The present invention makes it possible to realize a distal end cover of an endoscope, which is easy to be removed from a distal end member even with gloved fingers, and which is prevented from falling off the distal end member during use, and an endoscope to which a distal end cover is attached.

What is claimed is:
1. A distal end cover for use with an endoscope, the distal end cover being attached to a distal end member of the endoscope where the endoscope is provided with a raising base of an endoscope insertion portion, the distal end cover comprising:
    a body comprising:

a peripheral edge portion configured to form an opening that externally exposes a space in which the raising base is housed;

a planned-to-be-torn-apart section including a tear starting point disposed on a distal end of the peripheral edge portion, the planned-to-be-torn-apart section further including a first thin portion that is connected to the tear starting point, the first thin portion having a thickness less than a thickness of portions of the body that are adjacent to the planned-to-be-torn-apart section, the first thin portion being provided on one or more of an inside surface facing the opening or at least one side surface that connects the peripheral edge portion and the surface facing the opening; and an engagement protruding portion configured to be engaged with an outside surface of the distal end member, the engagement protruding portion projecting in a direction intersecting the outside surface to engage with the outside surface.

2. The distal end cover of an endoscope according to claim 1, wherein the first thin portion is provided extending proximally towards a proximal end of the body the.

3. The distal end cover of an endoscope according to claim 1, wherein the engagement protruding portion is provided on the at least one side surface.

4. The distal end cover of an endoscope according to claim 1, wherein the planned-to-be-torn-apart section further includes a second thin portion provided extending from the tear starting point to the first thin portion, on the inside surface.

5. The distal end cover of an endoscope according to claim 4, wherein the second thin portion is a groove provided on the inside surface.

6. The distal end cover of an endoscope according to claim 5, wherein the tear starting point, the second thin portion, and a portion of the first thin portion that form the planned-to-be-torn-apart section are disposed in positions away from a metal portion of the distal end member.

7. The distal end cover of an endoscope according to claim 1, wherein the engagement protruding portion includes at least two engagement protruding portions and the at least one side surface comprises at least two side surfaces each connecting the peripheral edge portion and the surface facing the opening; and each of the at least two engagement protruding portions is provided on one of the at least two side surfaces.

8. The distal end cover of an endoscope according to claim 1, wherein the distal end member further includes:

a notch surface formed distally relative to the engagement protruding portion, and an engagement groove engaged with the engagement protruding portion, wherein the body further including a depression provided between the inside surface of the body and the notch surface of the distal end member.

9. An endoscope comprising:

the distal end cover according to claim 1; and an engageable portion configured to engage with the engagement protruding portion of the body, the engageable portion being provided on the distal end member provided with the raising base of the endoscope insertion portion.

* * * * *